(12) United States Patent
Hübinette (10) Patent No.: US 9,826,902 B2
(45) Date of Patent: Nov. 28, 2017

(54) SENSOR GUIDE WIRE DEVICE AND SYSTEM INCLUDING A SENSOR GUIDE WIRE DEVICE

(75) Inventor: Ulrik Hübinette, Alunda (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 961 days.

(21) Appl. No.: 13/574,937

(22) PCT Filed: Jan. 17, 2011

(86) PCT No.: PCT/EP2011/050519
§ 371 (c)(1),
(2), (4) Date: Jul. 24, 2012

(87) PCT Pub. No.: WO2011/092069
PCT Pub. Date: Aug. 4, 2011

(65) Prior Publication Data
US 2012/0289808 A1    Nov. 15, 2012

Related U.S. Application Data

(60) Provisional application No. 61/298,655, filed on Jan. 27, 2010.

(30) Foreign Application Priority Data

Jan. 27, 2010   (SE) .................................... 1050086

(51) Int. Cl.
*A61B 5/00* (2006.01)
*A61B 5/0215* (2006.01)
(Continued)

(52) U.S. Cl.
CPC .......... *A61B 5/0002* (2013.01); *A61B 5/0215* (2013.01); *A61B 5/6851* (2013.01);
(Continued)

(58) Field of Classification Search
None
See application file for complete search history.

(56) References Cited

U.S. PATENT DOCUMENTS 5,568,815 A * 10/1996 Raynes et al. ................ 600/485
5,766,130 A *  6/1998 Selmonosky ................. 600/485
(Continued)

FOREIGN PATENT DOCUMENTS

| | | | |
|---|---|---|---|
| EP | 1 774 905 A1 | 4/2007 | |
| JP | 2010-538745 A | 12/2010 | |
| WO | WO 2008/100208 A1 | 8/2008 | |

OTHER PUBLICATIONS

Japanese Office Action and English language translation dated Sep. 30, 2014, 5 pgs.
Australian Office Action dated Feb. 28, 2014, (3 pgs.).

*Primary Examiner* — Jacqueline Cheng
*Assistant Examiner* — Jairo Portillo
(74) *Attorney, Agent, or Firm* — Foley & Lardner LLP (57) ABSTRACT

A sensor guide wire device (200) for intravascular measurements of a physiological variable in a living body is disclosed. The sensor guide wire (200) may comprise a sensor element (213) and a connector unit (220). The connector unit (220) is attachable to a signal converting device (310). The sensor element (213) provides the signal converting device (310) with a signal indicative of a physiological variable sensed by the sensor element (213). Furthermore, the connector unit (220) comprises a battery (222). A system (300) comprising the sensor guide wire device (200) and the signal converting device (310) is also disclosed.

19 Claims, 4 Drawing Sheets

(51) Int. Cl.
*A61M 25/09* (2006.01)
*A61B 5/01* (2006.01)

(52) U.S. Cl.
CPC ........... *A61M 25/09* (2013.01); *A61B 5/0017* (2013.01); *A61B 5/01* (2013.01); *A61B 5/02156* (2013.01); *A61B 2560/0214* (2013.01); *A61B 2560/045* (2013.01); *A61B 2562/225* (2013.01); *A61M 2025/09083* (2013.01); *A61M 2025/09175* (2013.01)

(56) References Cited

U.S. PATENT DOCUMENTS

| | | | |
|---|---|---|---|
| 6,167,763 B1 | 1/2001 | Tenerz et al. | |
| 6,585,660 B2 | 7/2003 | Dorando et al. | |
| 6,615,067 B2 | 9/2003 | Hock et al. | |
| 7,311,675 B2 * | 12/2007 | Peifer et al. | 600/587 |
| 8,425,416 B2 * | 4/2013 | Brister et al. | 600/309 |
| 2003/0114869 A1 | 6/2003 | Nash et al. | |
| 2006/0036184 A1 * | 2/2006 | Tenzer et al. | 600/485 |
| 2007/0078323 A1 | 4/2007 | Reggiardo et al. | |
| 2007/0106165 A1 * | 5/2007 | Tulkki | 600/486 |
| 2008/0200770 A1 | 8/2008 | Hubinette | |
| 2008/0200789 A1 * | 8/2008 | Brister et al. | 600/347 |
| 2008/0281168 A1 * | 11/2008 | Gibson et al. | 600/301 |
| 2008/0319290 A1 | 12/2008 | Mao et al. | |
| 2009/0005675 A1 * | 1/2009 | Grunwald et al. | 600/424 |
| 2009/0076360 A1 | 3/2009 | Brister et al. | |
| 2009/0124880 A1 * | 5/2009 | Smith | 600/373 |
| 2009/0171163 A1 * | 7/2009 | Mates | A61B 5/00 600/300 |
| 2010/0324403 A1 | 12/2010 | Brister et al. | |
| 2011/0071407 A1 * | 3/2011 | Hubinette et al. | 600/485 |

* cited by examiner (Prior art) Fig. 1

SENSOR GUIDE WIRE DEVICE AND SYSTEM INCLUDING A SENSOR GUIDE WIRE DEVICE

FIELD OF THE INVENTION

The invention generally relates to the area of medical devices. More particularly, the present invention concerns a sensor guide wire device for intravascular measurements of a physiological variable e. g. pressure or temperature, inside a living human or animal body, and also to a system for intravascular measurements of a physiological variable in a living body, in accordance to the preambles of the independent claims.

BACKGROUND OF THE INVENTION

In many medical procedures, medical personnel wish to monitor various physiological conditions that are present within a body cavity of a patient. These physiological conditions are typically physical in nature—such as pressure, temperature, rate-of-fluid flow—and provide the physician or medical technician with critical information as to the status of a patient's condition. The manner by which these types of parameters are measured and monitored should of course be as safe, as accurate and as reliable as possible.

Equipment and processes have therefore been developed for assisting medical personnel such as physicians or medical technicians in diagnosing physiological conditions of a patient. For example, sensor guide wires in which a sensor is mounted at the distal end of a guide wire have been developed. The sensor may, e.g., be an intra-vascular pressure sensor that is arranged to measure blood pressure at various points within the vasculature to facilitate locating and determining the severity of e.g. stenosis or other disruptors of blood flow within the vessels of the living body.

Figure 1:
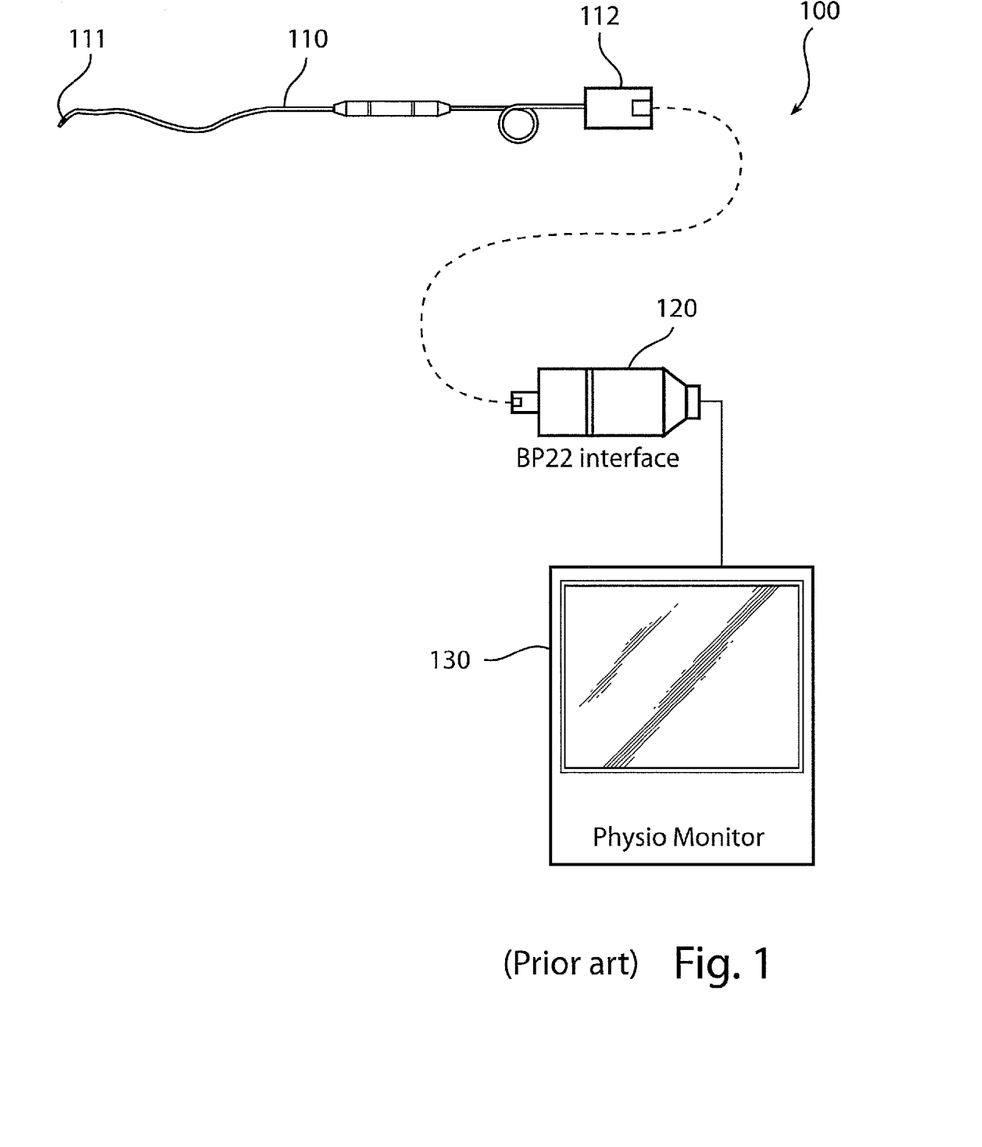
FIG. 1 is a schematic drawing depicting a previous connection scheme between a pressure-sensing guide wire and a physiology monitor.

With reference to FIG. 1, a typical intra-vascular pressure sensor-to-physiological monitor interface system 100 is illustrated. The arrangement comprises a sensor guide wire 110, a signal converting device 120, and a physiology monitor 130. The sensor guide wire 110 may comprise a sensor element 111 arranged at the distal end of the sensor guide wire 110. The sensor element 111 may be arranged to sense a physiological variable in a living body, such as a human or animal body. The sensor guide wire 110 is a disposable device which typically includes a connector 112 for connection to the signal converting device 120. The signal converting device 120 is arranged to interface the guide wire-mounted sensor element 111 to the physiology (e.g. blood pressure) monitor 130. The signal converting device 120 may be configured to receive a signal indicative of a physiological variable sensed by the sensor element 111 from the guide wire-mounted sensor element 111. Furthermore, the signal converting device 120 is configured to process the received signal such that a normalized signal to any of multiple different physiology monitors having potentially differing signal requirements can be forwarded to the physiology monitor 130. Thus, the signal converting device 120 is configured to convert the signal indicative of a physiological variable sensed by the sensor element to a signal according to an established standard, e.g. the standard set by the American National Standards Institute ("ANSI")/AAMI BP22-1994 (referred to the BP 22-standard in the following), which is receivable by the physiology monitor 130.

In the previously described intra-vascular pressure sensor-to-physiological monitor interface system 100, as shown in FIG. 1, the signal converting device 120 typically includes a battery (not shown) for powering the system. When such battery has been discharged, it must generally be replaced because otherwise disrupted readings could be the direct result of such discharged battery. Sometimes, the procedure of replacing the discharged battery with a fresh battery can be rather complex and/or time-consuming for the medical personnel who must perform this procedure.

WO-2008/100208 relates to a measurement system comprising a sensor wire provided with a physiological condition sensor at its distal end. The system is in particular related to a system where a transceiver unit, being connected to the sensor wire, is completely galvanically isolated from a physiology monitor. This is achieved by arranging an optical communication link for transferring the signal from the sensor to the physiology monitor. Thereby the equipment of WO-2008/100208 may be used during external defibrillation and that external devices, (e.g. the monitor) are protected against defibrillation shocks and the patient is not part of a conducting circuit.

U.S. Pat. No. 6,585,660 relates to a signal conditioning device for interfacing intravascular sensors, e.g. guide-wire mounted pressure sensors, to a physiology monitor. The signal conditioning device processor is herein power supplied by an excitation signal received from the physiology monitor.

The object of the present invention is to achieve an improved sensor guide wire device that obviates the need for complex and time-consuming battery replacement and that is less complex and thereby easy to manufacture.

SUMMARY OF THE INVENTION

It is with respect to the above considerations and object that the present invention has been made. The present invention seeks to mitigate, alleviate or eliminate one or more of the above-mentioned deficiencies and disadvantages singly or in combination. In particular, the inventor has realized that it would be desirable to achieve an improved sensor-to-physiological monitor system, which avoids the need of replacing a discharged battery of the signal converting device with a fresh battery.

It would also be advantageous to achieve a novel sensor guide wire, which contributes to the avoidance of said need of replacing a discharged battery of the signal converting device with a fresh battery.

To better address one or more of these concerns a sensor guide wire device and a system having the features defined in the independent claims are provided. Further advantageous embodiments of the present invention are defined in the dependent claims.

According to a first aspect of the invention, there is provided a sensor guide wire device for intravascular measurements of a physiological variable in a living body, the sensor guide wire device comprising a sensor element arranged to sense a physiological variable in a living body and a connector unit attachable to a signal converting device for providing the signal converting device with a signal indicative of a physiological variable sensed by the sensor element, wherein the connector unit comprises a power supply arranged to power the signal converting device when the connector unit is attached to the signal converting device.

The power supply preferably comprises at least one battery.

The connector unit is preferably positioned at a proximal portion of the sensor guide wire device and the sensor element is positioned at a distal portion of the sensor guide wire device.

The connector unit is provided with a connector, either a male or a female connector arranged to connect with a female connector, or male connector, respectively, of the signal converting device.

According to a second aspect of the invention, there is provided a system for intravascular measurements of a physiological variable in a living body, the system comprising a sensor guide wire device according to the first aspect of the invention and a signal converting device attachable to the sensor guide wire device via the connector unit of the sensor guide wire device.

The signal converting device may comprise a power supply monitoring device, which is arranged to monitor the power level of the power supply when the signal converting device is attached to the connector.

Alternatively, or additionally, the system may comprise a power supply monitoring device, which is attachable to the connector and which is further arranged to monitor the power level of the power supply when attached to the connector unit.

The signal converting device is arranged to convert the signal indicative of the physiological variable to a signal in accordance with an established standard. The established standard may preferably, but not necessarily, be the standard set by the American National Standards Institute ("ANSI")/AAMI BP22-1994, i.e. the BP 22-standard.

The system may further comprise a physiology monitor communicatively connectable to the signal converting device.

The physiology monitor may be connectable to the signal converting device via a wired or a wireless connection.

The present invention is based on the inventor's insight that the power supply, e.g. in the form of a battery, advantageously is placed in the connector unit, i.e. being an integral part of the sensor guide wire device. In other words, the battery is advantageously placed in that part of the sensor-to-physiological monitor interface system that is intended for a single use. That is, the battery is placed in the disposable part of the system, namely in the sensor guide wire. This is in contrast to previous intra-vascular pressure sensor-to-physiological monitor interface systems, e.g. WO-2008/100208, where the battery is placed within the signal converting device.

By placing the power supply in the disposable sensor guide wire part of the system, e.g. in the connector unit of the sensor guide wire device, once the fresh sensor guide wire is attached to the signal converting device its power supply will be fresh. Thus, there will no longer be a need for any complex battery replacement when the battery is discharged. Since the power supply of the sensor guide wire is most likely always fresh when it is attached or connected to the signal converting device, this also provides for a minimized or at least reduced risk of disrupted readings as a result of a discharged battery.

Furthermore, according to the present invention the signal converting device is arranged separately from the disposable connector unit and thus being non-disposable. This is advantageous in that the disposable parts of the system, i.e. the sensor guide wire device, the connector unit and also a wire connector and a cable, are then less complicated and less expensive to manufacture.

Generally, the various aspects of the invention may exhibit the same or similar advantages. Also, it should be appreciated that the various embodiments of the invention may exhibit the same or similar advantages.

These advantages and/or other aspects of the invention will be apparent from and elucidated with reference to the illustrative embodiments described hereinafter.

Generally, all terms used herein are to be interpreted according to their ordinary meaning in the technical field, unless explicitly defined otherwise herein.

SHORT DESCRIPTION OF THE APPENDED DRAWINGS

Embodiments of the present invention will now be described in more detail, reference being made to the enclosed drawings, in which.

DETAILED DESCRIPTION OF PREFERRED EMBODIMENTS OF THE INVENTION

The present invention will now be described more fully hereinafter with reference to the accompanying drawings, in which exemplifying embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Furthermore, like numbers refer to like elements throughout.

Various embodiments of the present invention are based on the inventor's realization that the power supply, e.g. in the form of a battery, can advantageously be placed in the connector unit, i.e. an integral part of the sensor guide wire device. That is, the battery can be advantageously placed in the part of the sensor-to-physiological monitor interface system that is individually calibrated before use.

As discussed above, by placing the power supply in the (disposable) sensor guide wire part of the system, there will no longer be any need for complex battery replacements when the battery is discharged as was needed in previous sensor-to-physiological monitor interface systems (FIG. 1) where the signal converting device was equipped with the battery.

Since the power supply of the sensor guide wire device will most probably always be fresh when it is connected to the signal converting device, this also provides for a minimized or at least reduced risk of disrupted readings as a result of a discharged battery. As will be further discussed below, in advantageous embodiments of the invention there is also provided a power supply monitoring device, which can be used for detecting whether the power supply is charged or discharged. Such power supply warning/detection mechanism can advantageously be used before the sensor-to-physiological monitor interface system is put in operation.

It is known to persons skilled in the art to mount a sensor on a guide wire and to position the sensor via the guide wire in a blood vessel in a living body, such as a human body, to detect a physical variable or parameter, e.g. pressure or temperature. The sensor can include elements that are directly or indirectly sensitive to the parameter. Numerous patents describing different types of sensors for measuring physiological parameters are owned by the applicant of the present patent application. For example, temperature could be measured by observing the resistance of a conductor having temperature sensitive resistance as described in U.S. Pat. No. 6,615,067. Another exemplifying sensor may be found in U.S. Pat. No. 6,167,763, in which blood flow exerts pressure on the sensor which delivers a signal representative of the exerted pressure.

In order to power the sensor and to communicate signals representing the measured physiological variable to external units disposed outside the body, one or more cables for transmitting the signals are connected to the sensor, and are routed along the guide wire to be passed out from the vessel to the external unit via a signal converting device also disposed outside the body. In addition, the guide wire is typically provided with a central metal wire (core wire) serving as a support for the sensor and enabling good maneuverability of the guide wire.

Figure 2:
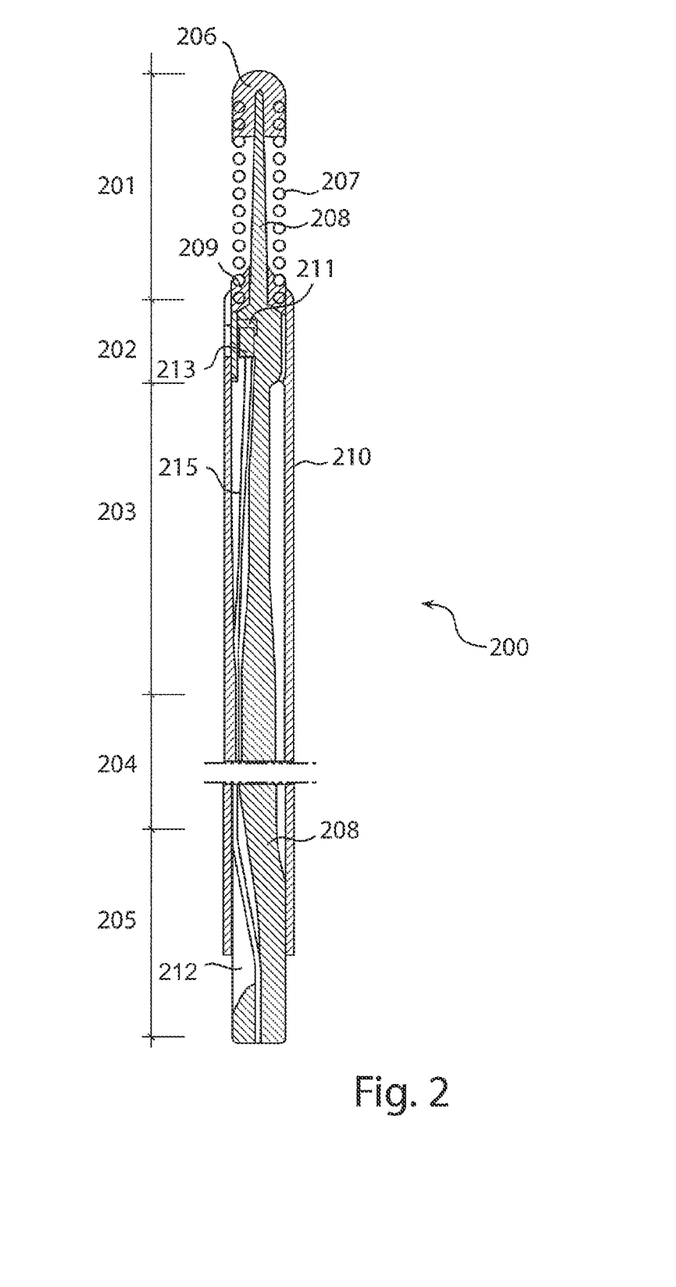
FIG. 2 illustrates an exemplary sensor element mounted on a sensor guide wire which is applicable in various embodiments of the present invention.

FIG. 2 shows an exemplifying sensor guide wire 200 in accordance with a design which is applicable to the various embodiments of the present invention. An exemplifying sensor element is mounted on a guide wire, i.e. a sensor guide wire 200. In the figure, the sensor guide wire 200 is divided into five sections, 201-205, for illustrative purposes. The section 201 is the most distal portion, i.e. that portion which is going to be inserted farthest into the vessel, and section 205 is the most proximal portion, i.e. that portion being situated closest to a not shown connector unit (reference sign 220 of FIG. 3). Section 201 comprises a radiopaque coil 207 made of e.g. platinum, provided with an arced tip 206. In the platinum coil and the tip, there is also attached a stainless, solid metal wire 208, which in section 201 is formed like a thin conical tip and functions as a security thread for the platinum coil 207. The successive tapering of the metal wire 208 in section 201 towards the arced tip 206 results in that the front portion of the sensor guide construction becomes successively softer.

At the transition between the sections 201 and 202, the lower end of the coil 207 is attached to the wire 208 with glue or alternatively, solder, thereby forming a joint. At the joint 209 a thin outer tube 210 commences and extends downwards to section 205. The tube 210 has been treated to give the sensor guide wire 200 a smooth outer surface with low friction. The metal wire 208 may be heavily expanded in section 202 and can, in this expansion, be provided with a slot 211 in which a sensor element 213 is arranged, e.g. a pressure gauge. The sensor element 213 typically requires electric energy for its operation. The expansion of the metal wire 208 in which the sensor element 213 is attached can decrease the stress exerted on the sensor element 213 in sharp vessel bends.

From the sensor element 213 there is arranged a signal transmitting cable 215, which typically comprises one or more electric cables. The signal transmitting cable 215 extends from the sensor element 213 to a (not shown) connector unit (see FIG. 3) being situated below the section 205 and outside the body. A supply voltage may be fed to the sensor via the transmitting cable 215 (or cables). The signals representing the measured physiological variable are also transferred along the transmitting cable(s) 215. The metal wire 208 may be substantially thinner in the beginning of section 203 to obtain good flexibility of the front portion of the sensor guide wire 200. In the end of section 203 and in the whole of section 204, the metal wire 208 can be thicker in order to make it easier to push the sensor guide construction 200 forward in the vessel. In section 205 the metal wire 208 is as coarse as possible to be easy to handle and is here provided with a slot 212 in which the cable 215 can be attached with e.g. glue.

Figure 3:
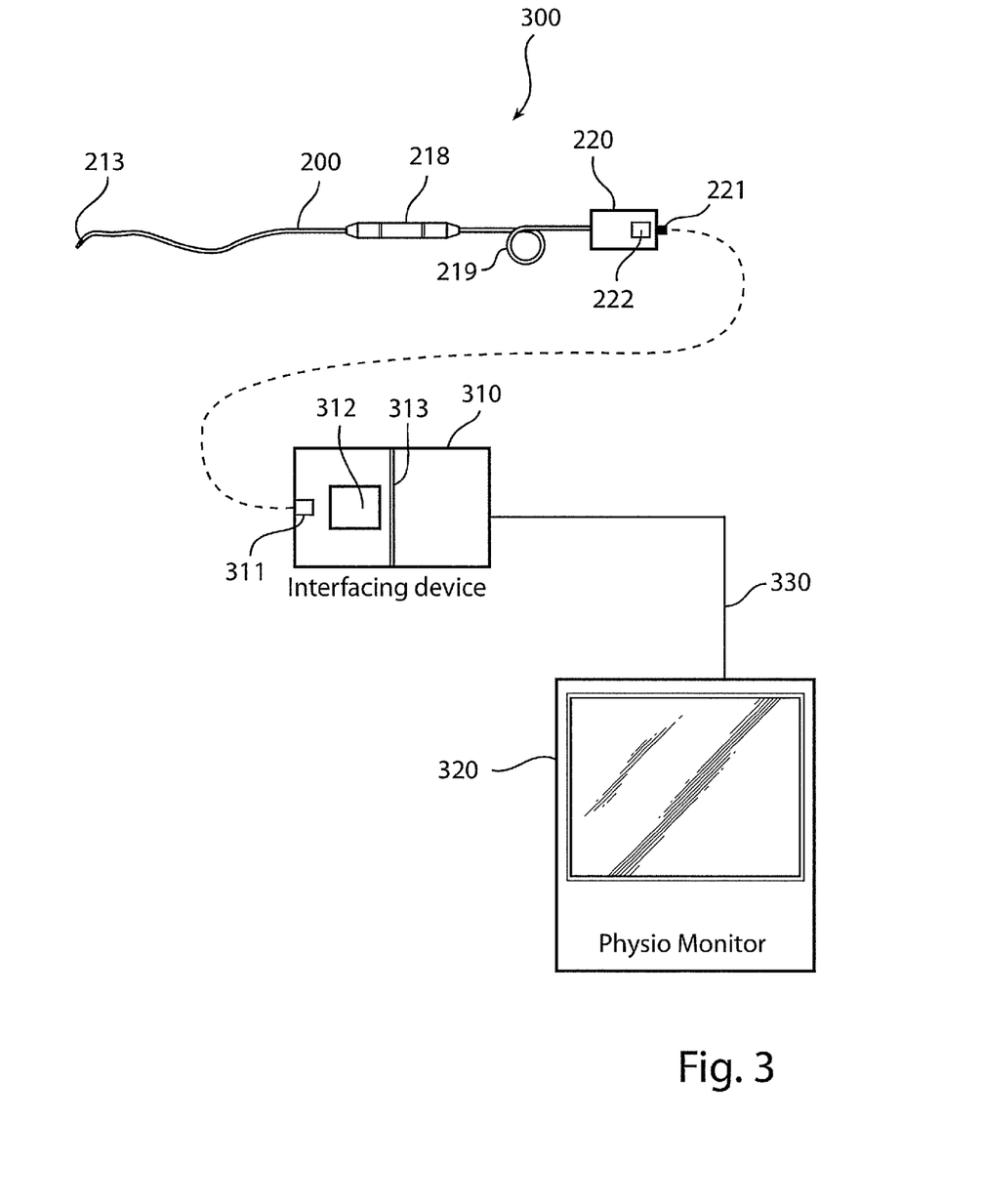
FIG. 3 illustrates a sensor-to-physiological monitor system according to an embodiment of the invention.

FIG. 3 shows a schematic overview of a sensor-to-physiological monitor system 300 illustrating the application of an exemplary embodiment of the present invention. The sensor-to-physiological monitor system 300 comprises a sensor guide wire 200, a signal converting device 310 and a physiology monitor 320. For example, the system 300 comprises a sensor guide wire, such as the sensor guide wire 200 shown in FIG. 2, for sensing or measuring a physiological condition, e.g. pressure, inside a patient, and to provide measured data to an external device, e.g. the physiology monitor 320.

The sensor guide wire 200 typically cannot be directly connected to the external monitor 320. Therefore, a signal converting device 310 interfaces the sensor guide wire 200 and the physiology monitor 320, respectively. Typically, the signal converting device 310 is arranged to convert a signal indicative of the physiological variable sensed by the sensor element 213 of the sensor guide wire 200 to a signal in accordance with an established standard, such as the BP 22-standard, which is receivable by the monitor 320.

With reference to FIG. 3, the sensor guide wire 200 is provided on the patient side. The sensor guide wire 200 is attachable to the signal converting device 310 via a wire connector 218, into which the proximal end of the sensor guide wire is inserted and attached, and a cable 219 electrically connecting the wire connector to the connector unit 220.

The connector unit 220 is attachable to the signal converting device 310 in such way that it can provide the signal converting device 310 with a signal indicative of a physiological variable sensed by the sensor element 213, when the sensor guide wire 200 is in use.

The signal converting device 310 is preferably provided with an optical communication link 313 for transferring the signal from the sensor to the physiology monitor. The optical communication link 313 is indicated in the figure by two vertical lines. When the sensor guide wire and connector unit are connected to the signal converting device these parts of the system are then completely galvanically isolated from the physiology monitor. Thereby the equipment may be used during external defibrillation and that external devices, (e.g. the monitor) are protected against defibrillation shocks and that no closed circuit that includes the patient is obtained. The optical communication link may be of the kind described in detail in WO-2008/100208.

Generally, the sensor guide wire 200 can provide the signal converting device 310 with a signal indicative of a physiological variable sensed by the sensor element 213 in any conventional manner which is known by persons skilled in the art. Therefore, this will not be discussed in greater detail herein. In this regard, it should also be appreciated that the sensor guide wire 200 to which the signal converting device 310 is attachable via the connector unit 220 and the composition of cables between the sensor element 213 and the signal converting device 310 vary in accordance with design considerations and functional requirements and this should, hence, be tested and evaluated for each specific case.

The connector unit 220 may comprise a male connector 221 for connection with a female connector 311 of the signal converting device 310. Alternatively, in another embodiment which is not illustrated in the drawings the connector unit 220 may comprise a female connector for connection with a male connector of the signal converting device 310. The male and female connectors, respectively, are constructed in such a way that the male connector can be inserted snugly into a receptacle (i.e. the female connector) to ensure a reliable physical and electrical connection.

The connector unit 220 comprises a power supply, preferably a battery 222. The power supply 222 is arranged to power the signal converting device 310 when the connector unit 220 is attached to the signal converting device 310. The battery 222 is placed within the connector unit 220. In other words, the battery 222 is an integral part of the connector unit 220. Since the sensor guide wire device is disposable, i.e. intended for a single use, it should be appreciated that the battery 222 will always be fresh, i.e. fully or at least sufficiently charged, before use. Accordingly, by placing the battery 222 in the sensor guide wire device part of the system, once the fresh sensor guide wire device is attached via the male 221/female 311 connectors to the signal converting device 310 its battery 222 will be fresh.

According to a preferred embodiment the sensor element is energized by the battery via the signal converting device when the sensor guide wire device is attached to said signal converting device. This is achieved via electrical connections through the connector unit and preferably the cable and wire connector, and cables running along the sensor guide wire.

With continuing reference to FIG. 3, the system 300 comprises, according to one embodiment, a power supply monitoring device for monitoring the power level of the power supply. This has the advantage of enabling detection of whether the power supply is charged or discharged. In the disclosed embodiment, the signal converting device 310 comprises a power supply monitoring device 312. The power supply monitoring device is arranged to monitor the power level of the power supply, i.e. battery 222, of the connector unit 220 when the connector unit 220 has been attached to the signal converting device 310. Preferably, but not necessarily, the power supply monitoring device 312 is operable to check the power level of the battery 222 immediately, or as soon as possible, after attachment to the connector 220. In this way, medical personnel who wish to monitor various physiological conditions of a patient can check the quality of the battery themselves, before putting the system 300 in operation, in order to avoid later disruptive readings that are the result of a discharged battery. The power supply monitoring device 312 is preferably adapted to generate a power level alert signal if said power level of the power supply is below a preset threshold and also provided with an indicator (not shown in the figures) arranged to visually display the current status of the power supply, i.e. to visually indicate if a power level alert signal has been generated.

Figure 4:
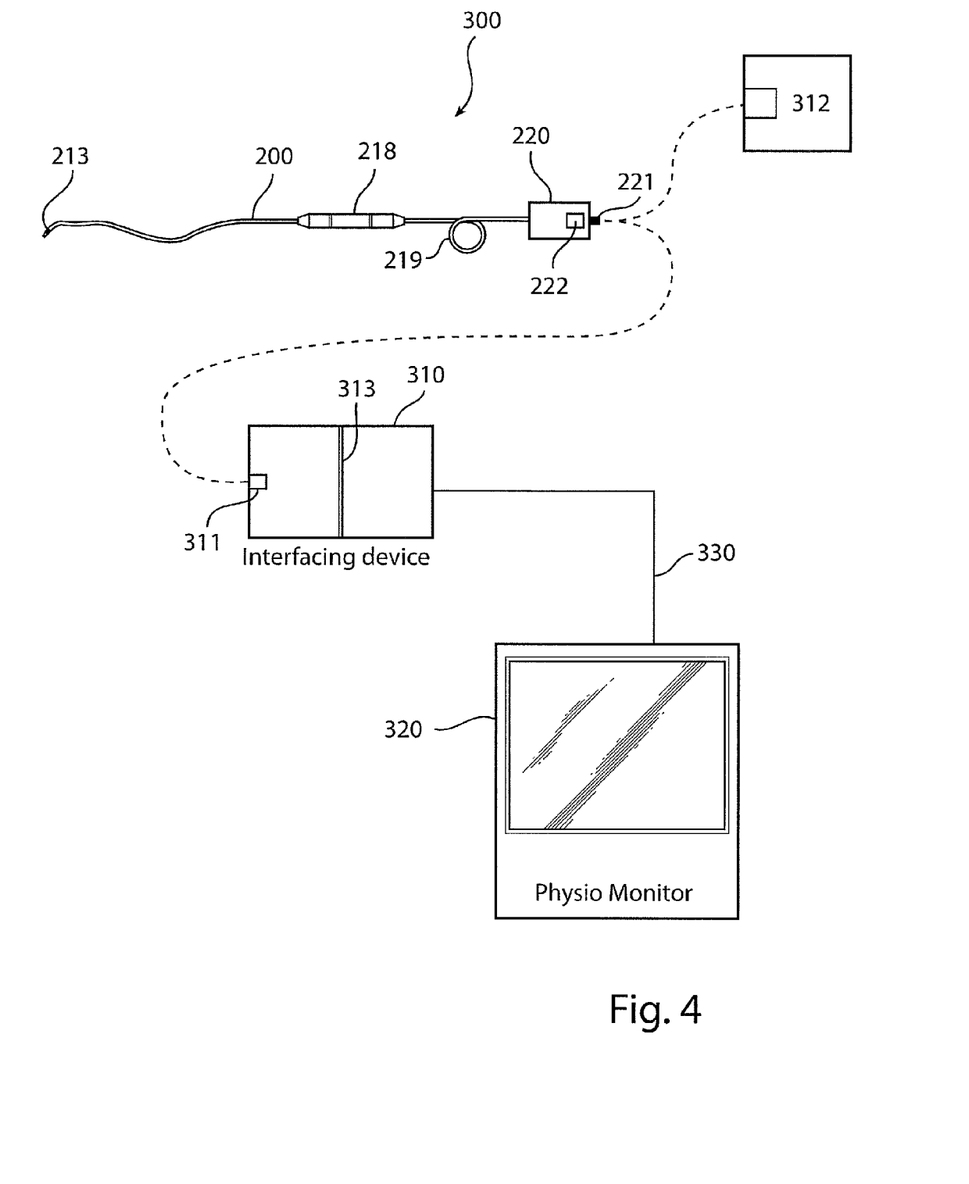
FIG. 4 illustrates a sensor-to-physiological monitor system according to another embodiment of the invention.

With reference to FIG. 4, an alternative embodiment of the power supply monitoring device is shown. Here, the power supply monitoring device 312 is not comprised in the signal converting device 310. Instead the power supply monitoring device 312 is an external device, which is separate from both the sensor guide wire device and the signal converting device 310. The power supply monitoring device 312 can be used for the sole purpose of monitoring or checking the power level of the battery 222 of the connector unit 220. By providing a separate power supply monitoring device 312 it is possible to perform the battery check before and even well before the sensor guide wire device is intended for use together with the signal converting device 310 and the monitor 320 of the system 300. Sensor guide wire manufacturers (or vendors) can hence check the battery quality before the sensor guide wires are shipped to the end customers (e.g. the medical personnel). This has the advantage that fewer malfunctioning or discharged batteries will ever reach the end customers. Accordingly, once the sensor guide wires that have been tested are put on the market, the batteries of these sensor guide wire devices will be sufficiently charged and, in turn, when these are put in use together with the signal converting device 310 and the monitor 320 of the system 300 there will be no or little risk of disruptive readings that are the result of discharged batteries. The power supply monitoring device 312, according to this embodiment, is preferably also adapted to generate a power level alert signal if said power level of the power supply is below a preset threshold and also provided with an indicator (not shown in the figures) arranged to visually display the current status of the 10 power supply, i.e. to visually indicate if a power level alert signal has been generated.

With continuing reference to FIGS. 3 and 4, the system 300 may further comprise a physiology monitor 320 from which medical personnel may monitor various physiological conditions of a patient sensed by the sensor element 213 of the sensor guide wire 200. Again, these physiological conditions are typically physical in nature—such as pressure, temperature, rate-of-fluid flow—and provide the physician or medical technician with critical information as to the status of a patient's condition. Based on this information, corrective measures can be taken by the medical technician, if deemed necessary or appropriate. The physiology monitor 320 can be connected to the signal converting device 310 either in a wired or a wireless fashion in any conventional manner which is known by persons skilled in the art. Therefore, this will not be discussed in further detail herein. For illustrative purposes only, the signal converting device 310 connects to the physiology monitor 320 via a connector cable 330 in the disclosed embodiment.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended patent claims. The mere fact that certain measures are recited in mutually different dependent claims does not indicate that a combination of these measured cannot be used to advantage. Rather, it should be appreciated that the invention relates to all possible combinations of features recited in the claims. Any reference signs in the claims should not be construed as limiting the scope.

The invention claimed is:

1. A sensor guide wire device comprising:
    a sensor guide wire configured to perform an intravascular measurement of a physiological variable in a living body, the sensor guide wire comprising at least one sensor element configured to sense the physiological variable in the living body; and
    a connector unit configured to be directly or indirectly connected to a proximal end of the sensor guide wire, the connector unit being physically attachable to a signal converter via electrical contacts, the connector unit being configured to provide the signal converter with a signal indicative of the physiological variable sensed by the sensor element, the signal converter being configured to convert the signal received from the connector unit into a processed signal that is receivable by a physiology monitor, wherein the connector unit comprises a housing and a power supply disposed in the housing, the housing of the connector unit being separate from a housing of the signal converter, wherein the housing of the connector unit is reversibly attachable to and detachable from the housing of the signal converter, wherein the connector unit is configured such that, when the housing of the connector unit is attached to the housing of the signal converter, a surface of the housing of the connector unit abuts a surface of the housing of the signal converter, and the power supply of the connector unit powers the signal converter via the electrical contacts, and wherein the sensor guide wire and the connector unit are disposable.

2. The sensor guide wire device according to claim 1, wherein said sensor element is energized by said signal converter when the connector unit is attached to said signal converter.

3. The sensor guide wire device according to claim 2, wherein said connector unit comprises a calibration memory that includes calibration data related to said sensor element.

4. The sensor guide wire device according to claim 1, wherein said connector unit comprises a calibration memory that includes calibration data related to said sensor element.

5. The sensor guide wire device according to claim 1, wherein the power supply comprises at least one battery.

6. The sensor guide wire device according to claim 1, wherein the connector unit is positioned at a proximal portion of the sensor guide wire.

7. The sensor guide wire device according to claim 1, wherein the connector unit comprises a male connector configured to connect with a female connector of the signal converter.

8. The sensor guide wire device according to claim 1, wherein the connector unit comprises a female connector configured to connect with a male connector of the signal converter.

9. The sensor guide wire device according to claim 1, wherein the signal converter is configured to process said signal such that the processed signal is receivable by any of multiple different physiology monitors having differing signal requirements.

10. The sensor guide wire device according to claim 1, wherein the sensor guide wire and the connector unit are heat-sterilizeable.

11. A system for intravascular measurements of a physiological variable in a living body, the system comprising:
    a sensor guide wire device according to claim 1,
    a signal converter attachable to the sensor guide wire device via the connector unit of the sensor guide wire device.

12. The system according to claim 11, wherein the signal converter comprises a power supply monitor configured to monitor a power level of the power supply when the signal converter is attached to the connector unit, and to generate a power level alert signal if said power level of the power supply is below a preset threshold.

13. The system according to claim 11, further comprising: a power supply monitor, which is attachable to the connector unit and which is configured to monitor a power level of the power supply when attached to the connector unit, and to generate a power level alert signal if said power level of the power supply is below a preset threshold.

14. The system according to claim 11, wherein the signal converter is configured to convert said signal indicative of the physiological variable to a signal in accordance with an established standard.

15. The system according to claim 14, wherein the established standard is a BP 22-standard.

16. The system according to claim 11, wherein said signal converter comprises an optical communication link configured to achieve a communication link having no galvanic connection between a signal processing part of the signal converter and a physiology monitor connectable to said signal converter.

17. The system according to claim 11, further comprising:
    a physiology monitor communicatively connectable to the signal converter.

18. The system according to claim 17, wherein the physiology monitor is connectable to the signal converter via a wired connection.

19. The system according to claim 17, wherein the physiology monitor is connectable to the signal converter via a wireless connection.

* * * * *